United States Patent [19]

Periana et al.

[11] Patent Number: 5,306,855
[45] Date of Patent: * Apr. 26, 1994

[54] CATALYTIC PROCESS FOR CONVERTING LOWER ALKANES TO ESTERS, ALCOHOLS, AND TO HYDROCARBONS

[75] Inventors: Roy A. Periana, San Jose; Douglas J. Taube, Hayward; Henry Taube, Stanford; Eric R. Evitt, Mountain View, all of Calif.

[73] Assignee: Catalytica, Inc., Mountain View, Calif.

[*] Notice: The portion of the term of this patent subsequent to Aug. 3, 2010 has been disclaimed.

[21] Appl. No.: 799,446

[22] Filed: Nov. 27, 1991

Related U.S. Application Data

[63] Continuation-in-part of Ser. No. 656,910, Feb. 15, 1991, Pat. No. 5,233,113, and Ser. No. 766,200, Sep. 26, 1991, abandoned.

[51] Int. Cl.$^5$ ............................................. C07C 2/00
[52] U.S. Cl. ................................... 585/500; 585/469; 585/638; 585/733; 585/943; 560/302; 560/304; 560/305; 560/318
[58] Field of Search ............... 585/638, 733, 500, 469, 585/310, 314, 423; 560/302, 304, 305, 318; 423/304, 573

[56] References Cited

U.S. PATENT DOCUMENTS

| | | | |
|---|---|---|---|
| 3,702,886 | 11/1972 | Argauer et al. | 423/328 |
| 3,894,107 | 7/1975 | Butter et al. | 260/688 |
| 3,928,483 | 12/1975 | Chang et al. | 260/688 R |
| 3,979,470 | 9/1976 | Firnhaber et al. | 260/658 R |
| 3,979,472 | 9/1976 | Butter et al. | 260/668 R |
| 4,373,109 | 2/1983 | Olah | 585/640 |
| 4,453,434 | 9/1985 | Chang | 585/310 |
| 4,523,040 | 6/1985 | Olah | 568/671 |
| 4,524,234 | 6/1985 | Kaiser | 585/638 |
| 4,579,996 | 4/1986 | Font Friede et al. | 585/642 |
| 4,687,875 | 8/1987 | Currie et al. | 585/469 |
| 4,804,797 | 2/1989 | Minet et al. | 585/500 |
| 4,864,073 | 9/1989 | Han et al. | 585/943 |
| 4,864,074 | 9/1989 | Han et al. | 585/943 |

OTHER PUBLICATIONS

A. E. Shilov and A. A. Shteinman, "Activation of Saturated Hydrocarbons by Metal Complexes in Solutions," *Kinetka i Kataliz*, 18:1129-1145 (1977).
Sen et al., "Palladium (II) Mediated Oxidative Functionalization of Alkanes and Arenes," *New Journal of Chemistry* 13:756-760 (1989).
Vargaftik et al., "Highly Selective Partial Oxidation of Methane to Methyl Trifluoroacetate," *Journal of the Chemical Society, Chemical Communications* pp. 1049-1050 (1990).
Olah et al., "Superacid-Catalyzed Oxygenation of Alkanes," *Angew, Chem. Int. Ed.*, 17:909-931 (1978).
Sen et al., "Homogeneous Palladium Mediated Oxidation of Methane," *Platinum Metals Review*, 35:126-132 (1991).

(List continued on next page.)

*Primary Examiner*—Asok Pal
*Assistant Examiner*—P. Achutamurthy
*Attorney, Agent, or Firm*—Morrison & Foerster

[57] ABSTRACT

This invention is a process for converting lower alkanes into their corresponding esters and optionally into various intermediates (such as alcohols) and other liquid hydrocarbons. The alkanes are oxidatively converted to oxy-esters at high selectivity and conversion and at practical reaction rates using at least catalytic amounts of certain class "B" metals and/or metal ions defined by the Pearson definition as "soft" or "borderline". Desirable catalysts comprise such metals as Pd, Tl, Pt, Hg, and Au. If so desired, the alkyl oxy-esters may be converted to alcohols or other intermediates such as alkyl halides. The oxy-esters, alcohols, and other intermediates may optionally be converted to liquid hydrocarbons such as gasoline.

58 Claims, No Drawings

OTHER PUBLICATIONS

Phillips and Williams, *Inorganic Chemistry*, pp. 459–477 (1966).

Huheey, *Inorganic Chemistry*, pp. 276–290 (1978).

Kao et al., "Low Temperature, Palladium (II) Catalyzed, Solution-Phase Oxidation of Methane to Methanol", J. Amer. Chem. Soc. vol. 113, 701–703 (1991).

Gretz et al., "Carbon–Hydrogen Bond Activation by Electrophydic Transition Metal Compounds. Palladium (II)-Mediated Oxidation of Arenes and Alkanes Including Methane": J. Amer. Chem. Soc., vol. 109, 8109–8111 (1987).

Rudakov et al., "Oxidation Kinetics of Saturated Hydrocarbons in the Pd(II)–$H_2SO_4$ and $NO_2^+$–$H_2SO_4$ Systems": Doklady Akad. Nauk SSSR, vol. 224, No. 1, pp. 153–156 (1975).

Tret'yakov et al., "Ruthenium (IV) Complexes: Homogeneous and Heterogeneous Catalysts for the Oxidation of Unsaturated Hydrocarbons", Doklady Akad. Nauk SSSR, vol. 245, No. 5, pp. 1135–1138.

CATALYTIC PROCESS FOR CONVERTING LOWER ALKANES TO ESTERS, ALCOHOLS, AND TO HYDROCARBONS

RELATED APPLICATIONS

This is a continuation-in-part of U. S. Ser. No. 07/656,910, filed Feb. 15, 1991, to "CATALYTIC PROCESS FOR CONVERTING LOWER ALKANES TO ESTERS", by Roy A Periana, Eric R. Evitt, and Henry Taube, now U. S. Pat. No. 5,233,173, and also of U. S. Ser. No. 07/766,200, filed Sept. 26, 1991, to "PROCESS FOR SELECTIVE OXIDATION OF ALKANES AND ARENES", by Roy A. Periana, now abandoned, the entirety of which are incorporated by reference.

FIELD OF THE INVENTION

This invention is a process for converting lower alkanes into their corresponding esters and optionally into various intermediates (such as alcohols) and other liquid hydrocarbons. The alkanes are oxidatively converted to oxy-esters at high selectivity and conversion and at practical reaction rates using at least catalytic amounts of certain class "B" metals and/or metal ions defined by the Pearson definition as "soft" or "borderline". Desirable catalysts comprise such metals as Pd, Tl, Pt, Hg, and Au. Mercury is most desired. If so desired, the alkyl oxy-esters may be converted to alcohols or other intermediates such as alkyl halides. The oxy-esters, alcohols, and other intermediates may optionally be converted to liquid hydrocarbons such as gasoline.

BACKGROUND OF THE INVENTION

The countries of North America currently import significant portions of their needed liquid hydrocarbons from Asia and Africa. Natural gas is abundant on the North American continent but is often present in remote locations. Although natural gas may be liquified and transported for subsequent use, appropriate refrigeration and compression equipment and transportation are quite expensive. Additionally, there are few economically viable technologies available for converting gaseous hydrocarbons to higher molecular weight liquid form materials. This invention includes a highly effective ctalytic step useful in converting methane and other lower alkanes to another, more reactive form which may then be converted to normally liquid hydrocarbons.

It is generally accepted that conversion of methane into a reactive intermediate is the most difficult step in the overall conversion of methane into higher molecular weight hydrocarbons (see, for instance, A.E. Shilov and A. A. Shteinman, "Activation of Saturated Hydrocarbons by Metal Complexes in Solution", *Kinetika i Kataliz*, Vol. 18, No. 5, pp. 1129-1145, 1977).

Several documents disclose a variety of methods for activating methane to produce other higher molecular weight materials.

Mobil Oil Corporation is assignee in several U.S. patents using sulfur or certain sulfur-containing compounds as the reactants in non-catalytic reactions with methane to produce methyl intermediates which can then be converted to higher molecular weight hydrocarbons.

In U. S. Pat. No. 4,543,434 Chang teaches a process using the following steps:

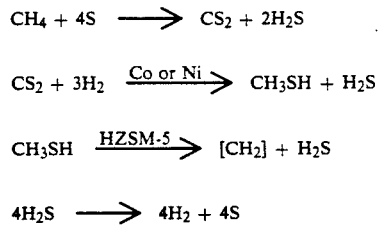

where "[CH$_2$]" is a hydrocarbon having at least two carbon atoms.

Another Mobil disclosure (U. S. Pat. No. 4,864,073 to Han et al.) suggests a carbonyl sulfide-based process in which methane and carbonyl sulfide are contacted in the presence of ultraviolet light under conditions sufficient to produce CH$_3$SH. No other reaction initiators are said to be present. The reaction scheme is shown to be:

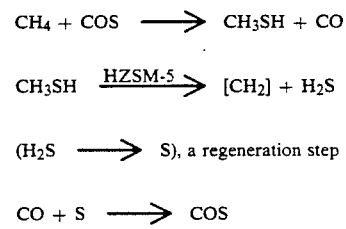

The selectivity of the first reaction is said to be high, i.e., around 81%; however, the conversion appears to be quite low.

A disclosure similar to that in Chang is found in Mobil's U.S. Pat. No. 4,864,074 to Han et al. As in Chang, the methane is contacted with sulfur. The process conditions are changed, however, so that either CS$_2$ or CH$_3$SH is formed. These sulfur compounds may then be converted in the presence of the preferred HZSM-5 zeolite catalyst to produce hydrocarbons having two or more carbon atoms. Also, as was the case with Chang, the step of contacting the methane to produce a methylsulfur compound is performed in the absence of a catalyst.

Other methods are known for producing substituted methanes which are suitable for further reaction to heavier hydrocarbons. A thermal methane chlorination process is shown in U.S. Pat. No. 4,804,797 to Minet et al. A similar process is disclosed in U.S. Pat. No. 3,979,470 to Fimhaber et al. although a preference for C$_3$ hydrocarbon feeds is expressed.

One method shown in U.S. Pat. No. 4,523,040 to Olah utilizes either a solid strongly acidic catalyst or a supported Group VIII metal (particularly platinum and palladium) in the gas phase halogenation of methane to produce methyl halides. The patent indicates that monohalides are produced in 85% to 99% selectivity. Olah suggests that subsequent or concurrent catalytic hydrolysis produces methyl alcohol and/or dimethyl ether. Production of methyl oxy-esters is not shown.

The reaction of methane with palladium (II) acetate in trifluoroacetic acid to effect the trifluoroacetoxylation of methane is shown in Sen et al., "Palladium (II) Mediated Oxidative Functionalization of Alkanes and Arenes", *New Journal of Chemistry* (1989), Vol. 13, No. 10-11, pp. 756-760. A yield of 60% based on palladium was reported when the reaction was practiced using methane as the reactant. Consequently, the reaction with methane utilized palladium as a reactant and not as a catalyst. The extent of methane conversion, selectivity, and reaction rates were not stated.

The Sen et al. article has been criticized in Vargaftik et al., "Highly Selective Partial Oxidation of Methane to Methyl Trifluoroacetate", *Journal of the Chemical Society, Chemical Communications* (1990), pp. 1049–1050, to the extent that the results were not found to be reproducible. Vargaftik et al. discloses the catalytic oxy-esterification of methane to methyl trifluoroacetate with cobalt in trifluoroacetic acid but shows that palladium is not even suitable for stoichiometric methane oxidation in that process. With Pd, less than 0.1% yield of methyl trifluoroacetate based on palladium (II) trifluoroacetate was obtained.

The Varaftik et al. article discloses that although palladium is ineffective for the conversion of methane to methyl trifluoroacetate, $Co^{III}$ can be used for this reaction. The $Co^{III}$ is said to be catalytic in the presence of oxygen. The rate of the reaction was very low, $2.5 \times 10^{-11}$ mol/cc sec, (or four to five orders of magnitude away from typical commercial rates of about $10^{-6}$ mol/cc.sec). Only four turnovers of the Co ion were disclosed. The extent of methane conversion was not stated. In addition to Co, other metals were suggested which were said to allow stoichiometric oxidation of methane to methyl trifluoroacetate in varying yields (based on amount of metal charged): Mn (30%), Cu (0.1%), and Pb (10%).

A later publication by Sen et al ("Homogeneous Palladium (II) Mediated Oxidation of Methane", *Platinum Metals Review*, (1991), Vol 35, No. 3, pp. 126–132) discloses a catalytic system using palladium as the catalyst, peroxytrifluoroacetic acid as the oxidant, and a mixture of trifluoroacetic acid and trifluoroacetic anhydride as the solvent. The reaction rate was low ($4.2 \times 10^{-9}$ mol/cc.sec) and only 5.3 turnovers of Pd were observed. The extent of methane conversion and selectivity were not stated.

None of these disclosures appear to show a process in which a lower alkane is oxidized to an oxy-ester intermediate using our class of catalysts and acids nor do they show a process combining that step with a step in which the oxy-ester intermediates so-produced are then converted into heavier liquid hydrocarbons. These disclosures further do not show processes achieving high conversion and selectivity for the catalytic oxidation of methane to methyl oxy-esters, particularly at practical reaction rates.

SUMMARY OF THE INVENTION

This invention is a catalytic oxidation process for the conversion of lower alkanes into alkyl oxy-esters which alkyl oxy-esters may be converted into hydrocarbons (desirably in the gasoline boiling rante) or alcohols. The alcohols may also be converted into hydrocarbons via a process such as oligomerization or the like.

The first step is catalytic and involves the contacting of a lower alkane (such as methane) with an acid, a catalyst in at least a catalytic amount comprising a Class "B" metal from the Mendeleev table and/or Pearson "soft" and "borderline" metal cations, and an oxidizing agent. The Class "B" metals are as described in Inorganic Chemistry, C. S. G. Phillips and R. S. P. Williams, Oxford University Press, 1966 at pp. 459–477. The so-called Pearson definitions of "soft" and "borderline" metal ions used in this disclosure may be found at pages 276 to 290 of Inorganic Chemistry, James E. Huheey, Harper and Row Publishers, Second Edition, 1978. The reaction may take place at low pressures and temperatures. The preferred metal catalysts are selected from Pd, Tl, Pt, Hg, and Au; most preferred is Hg. The preferred oxidizing agent is oxygen and/or $H_2SO_4$. The alkane is converted to an alkyl oxy-ester of the acid which is relatively inert to further oxidation under the reaction conditions.

The esters produced in the first step may then be converted to alcohols or to other suitable intermediates. This step may be used to regenerate the acid for recycle and reuse in the first step.

The alcohols or other intermediates may then be converted to higher hydrocarbons, preferably suitable for direct use as a fuel but at least suitable for further processing to higher hydrocarbons or chemicals. Of course, the alcohols can also be used directly as a fuel.

DESCRIPTION OF THE INVENTION

As noted above, this invention includes both the overall process for producing alcohols or higher hydrocarbons and the individual step of esterifying lower alkanes such as methane.

The overall process, using methane as an example of a lower alkane, may be outlined in the following fashion:

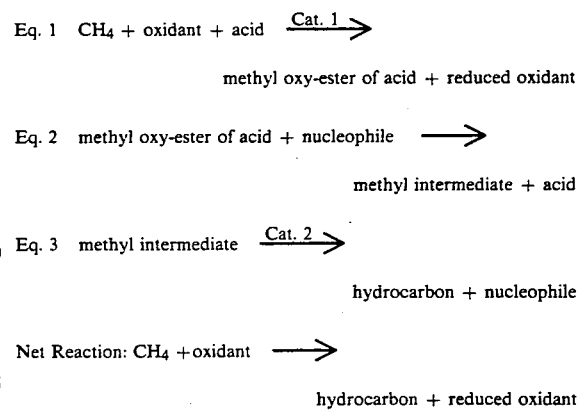

First Step

The first step (utilizing the reaction of Eq. 1) involves contacting methane with an acid and an oxidizing agent in the presence of a catalyst. The acid HX (where X is the acid's anion) may be an organic or inorganic acid such as $HNO_3$, $H_2SO_4$, $CF_3CO_2H$, $CF_3SO_3H$, $H_3PO_4$, HPA's (heteropolyacids), $B(OH)_3$ or the like, anhydrides of these acids such as $H_4P_2O_7$, $H_2S_2O_7$ or the like, and mixtures of two or more of these acids or these acids and anhydrides. The preferred acids are strong inorganic acids (pKa <2.0) and especially preferred are $H_2SO_4$ and $CF_3SO_3H$. For greatest efficiency the acids should be oxidation resistant: they should not be oxidized by the catalyst metal in the noted reaction medium. If such an oxidation were to occur, it would obviously result in destruction of the acid and need for additional acid processing. In addition to acting as a reactant, the acid may also be used in excess, and, in some cases as an oxidant, thereby acting as reactant (to form the oxy-ester), solvent, and sometimes, oxidant.

The oxidizing agent generally may be any oxidant capable of oxidizing the reduced form of the metal catalysts, e.g., a halogen (such as $F_2$, $Cl_2$, $Br_2$, $I_2$), $HNO_3$, perchloric acid, hypochlorites (such as NaOCl), peroxy compounds (such as $H_2O_2$, $CH_3CO_3H$, $K_2S_2O_8$), $O_2$ or $O_3$, $SO_3$, $NO_2$, $H_2SO_4$, cyanogen, etc. Oxygen is preferred because of its ready availability and low cost. $H_2SO_4$ is a desirable oxidant since the regeneration of the $SO_2$ produced is well known technology. Where $O_2$ is the oxidant, the manner of accomplishing Eq. 1 is as follows:

$$CH_4 + \tfrac{1}{2}O_2 + HX \rightarrow CH_3X + H_2O \qquad \text{Eq 1a}$$

Where $H_2SO_4$ is both the oxidant and the acid, the process for accomplishing Eq. 1 is as follows:

$$CH_4 + 2H_2SO_4 \rightarrow CH_3OSO_3H + 2H_2O + SO_2 \qquad \text{Eq 1b}$$

Where $SO_3$ is the oxidant and $H_2SO_4$ is the acid, the process for accomplishing the reaction of Eq. 1 is as follows:

$$CH_4 + SO_3 + H_2SO_4 \rightarrow CH_3OSO_3H + SO_2 + H_2O \qquad \text{Eq 1c}$$

Where $O_2$ is the oxidant and $CF_3SO_3H$ is the acid, the process for accomplishing the reaction of Eq. 1 is as follows:

$$CH_4 + \tfrac{1}{2}O_2 + CF_3SO_3H \rightarrow CH_3OSO_2CF_3 + H_2O \qquad \text{Eq 1d}$$

Since this is an oxidation process, the chemical oxidizing agent may be replaced with an electrochemical system. Where the oxidation is carried out electrochemically, the process for accomplishing the reaction of Equation 1 (at the anode) is as follows:

$$CH_4 + HX \rightarrow CH_3X + 2H^+ + 2e^- \qquad \text{Eq. 1e}$$

The catalyst used in Eq. 1 is one or more metals selected from the Class "B" metals of the Mendeleev Table and/or metals ions that are characterized as "soft" or "borderline" by the Pearson definitions. Thus, the metal ions are selected from the following: Cu, Zn, Pd, Ag, Cd, In, Sn, Sb, Te, Pt, Au, Hg, Tl, Pb, Bi, Ga, Ge, As, Po, Rh, Ir, Os, and Ru. The stable high oxidation states of these metals are characterized by a relatively high affinity for binding to "soft" polarizable ligands. Thus, these metals bind well to organic ligands since these species are "soft" and polarizable and tend to show the following order of binding (and insolubility) to the halogens: $I > Br > Cl > F$. Another important characteristic of these metals is the relative inefficiency with which these metals undergo one-electron reductions while still allowing efficient two-electron reductions. For example, $Au^{III}$, $Hg^{II}$, $Tl^{III}$, $Pd^{II}$, $Pt^{II}$ and $Pt^{IV}$ are not readily reduced to the $M^{n-1}$ oxidation state but are readily reduced to the $M^{n-2}$ states. Thus, for example, $Hg^{2+}$ reduces to produce $Hg_2^{2+}$ (a net $2e^-$ change) and $Hg^+$ is not a known species. (This is in stark contrast to metals such as $Co^{III}$ and $Mn^{III}$ which readily undergo $1e^-$ reduction by one-electron changes to produce the $M^{n-1}$ ions.) Strong acids (desired for heterolytic reactions) and the corresponding anions are resistant to oxidation and more easily oxidized by one-electron than two-electron processes. Thus, the Class "B" and/or "soft" metal ions do not readily oxidize strong acid solvents or the corresponding anions but can still allow efficient reaction of methane via a two-electron heterolytic process.

One such metal ion, $Pd^{2+}$, is a powerful oxidant ($E^0$ $Pd^{2+}/Pd^0 = 0.98$ V vs. NHE), and is characterized as a "soft" metal ion by the Pearson definition. Consistent with its classification as a "soft" metal ion and high ionization potential (19.42 eV), $Pd^{2+}$ allows facile reactions with alkanes ("soft" including methane. Consistent with these "soft" properties of $Pd^{2+}$ are the well known reactions of $Pd^{2+}$ with arenes (palladation) to produce isolable phenyl-palladium species. These phenyl-palladium species further react to produce functionalized aryl species, including aryl esters, presumably by a similar process that occurs in the formation of methyl esters from methyl-palladium species. This metallation reaction of arenes has been relatively well studied compared to the corresponding reaction with alkanes. The initial important reaction with arenes is thought to proceed via a heterolytic electriphilic CH bond activation, Eq 6, and since this is similar to the processes proposed for reaction with alkanes (See, Periana et al and Sen et al, above), could serve as a good model for electrophilic reactions with alkanes, Eq 7.

$$C_6H_6 + Pd^{2+} \rightarrow C_6H_5\text{-}Pd^+ + H^+ \qquad \text{Eq 6}$$

$$CH_4 + Pd^{2+} \rightarrow CH_3\text{-}Pd^+ + H^+ \qquad \text{Eq 7}$$

Due to the expense and slow reaction rates of Pd in the conversion of methane to methyl esters, the selection of other more active metals for methane activation is an important goal for the development of an economic process based on the heterolytic electrophilic conversion of methane to methyl esters. Using the intrinsic chemical properties of Pd discussed above as guidelines, other class "B", "soft" metal ions with oxidation potentials $>0.1$ volts were identified as candidates for the conversion of methane to methyl esters: $Au^{III}$, $Tl^{III}$, $Pt^{IV}$, $Pt^{II}$, $Hg^{II}$, $Cu^{II}$, $Ag^{I}$, $Bi^{IV}$, $Bi^{III}$, $Pb^{IV}$, $Pb^{II}$, $Rh^{III}$, $Sn^{IV}$, $Sn^{II}$, $Sb^{V}$, $Sb^{III}$, $Te^{IV}$, $Te^{III}$, $Ir^{III}$; $Ru^{III}$, $Ru^{IV}$, $Ru^{VI}$, $Ru^{VII}$, and $Ru^{VIII}$. Importantly, certain of these metal ions ($Tl^{III}$, $Au^{III}$, $Pt^{II}$, $Hg^{II}$, $Pb^{IV}$) are known to react with arenes by electrophilic mechanisms.

We have found that $Hg^{II}$, $Tl^{III}$, $Pt^{IV}$, $Pt^{II}$ and $Au^{III}$ are also effective ions for the selective oxidation of methane to methyl esters. Of these, $Hg^{II}$ is the most effective, exhibiting much higher activity than $Pd^{II}$, and is significantly less expensive and is especially reactive in $H_2SO_4$. The stoichiometry of the reaction when using $H_2SO_4$ is shown in Eq 1 b above.

The form in which the catalyst is introduced to the reaction medium is not particularly important; the requirements being only that it be in a form allowing oxidant, acid, and reactant access to the metal and that the form not restrict the ability of the catalytic metal to vary between oxidation states during the reaction. For instance, the metal may be introduced as a metal, salt, or complex into a liquid reaction medium. The catalytic metal (or metals) may be placed on the usual catalyst supports provided that the supports do not interfere with the requirements listed above. We have found that introducing the metal to the liquid reaction medium in a form which produces a homogeneous catalyst is very desirable. The metal may be introduced to the liquid reaction medium in a convenient form such as the salt of the acid used in Eq. 1, although that is not required. The metallic form of the catalyst may also be used. The catalyst metal concentration must be present in at least a catalytic amount; amounts of metal ranging between 50 ppm and 1.0% by mole of the total liquid present are effective although we have found no intrinsic limitation on the metal concentration. If the metal is to be used as a reactant rather than as a catalyst, then substantially larger amounts of the metal may be added. The reaction rate is related to the concentration of the catalytic metal; higher rates result from higher metal concentration.

The esterification process conditions used in the first step are as follows:

a. temperature is greater than 50° C., preferably 50° C. to 300° C., and most preferably 95° C. to 200° C.;

b. methane is added at a pressure above about 50 psig, preferably above about 300 psig, and most preferably above about 450 psig; and c. oxidant (whether pure or with other inert diluents) is added in an amount sufficient to support the reaction.

These conditions result in production of the alkyl oxy-ester of the acid in a molar amount greater than the molar amount of the catalyst metal charged in the reactor therefore giving a truly catalytic process.

The most preferred reaction situation for accomplishing Eq. 1 above is thus: the reaction is carried out in sulfuric acid, which acts as the solvent, reactant and oxidant. The concentration of Hg is as discussed generically above. The Hg is typically introduced into the reaction mixtures as $HgSO_4$ but any form of Hg is acceptable; e.g. $HgCl_2$, $Hg_2SO_4$, $Hg(NO_3)_2$, $Hg(CH_3)_2$, $Hg(C_6H_5)_2$, Hg metal, Hg amalgams with various metals, etc. Although the metallic form of the metal permits a reaction to occur, the ionic form is presumed to be the catalytically active state and reactions with metallic Hg likely proceed first by oxidation of the metal to the ionic state. Importantly, metallic Hg is not produced in the reaction and the reaction remains homogeneous independent of the form of Hg added to the reaction. The yield of the reaction when using Hg is sensitive to the concentration of the sulfuric acid and lower acid concentration results in lower yields. However, reaction does occur in 90% sulfuric acid and may occur in solutions as low as 50%. The fastest reactions and highest yields have been observed in 100% sulfuric acid. The reaction also occurs in sulfuric acid containing excess $SO_3$ (oleum). However, since the water generated in the reaction (Eq 1) must be removed (to prevent hydrolysis of the $CH_3OSO_3H$ and dilution of the sulfuric acid) a preferred concentration is about 96% $H_2SO_4$, since this concentration can readily be maintained by removal of water through simple distillation. The reaction may also be controlled to run at any desired concentration of $H_2SO_4$ by continous, controlled addition of $SO_3$ to the reaction mixture. This addition step prevents the build-up of water and may allow high conversion of the $H_2SO_4$ to the product methyl sulfate.

It is desirable to use $O_2$ as the oxidant in conjunction with $H_2SO_4$ as the reaction medium. This reaction is shown as Eq. 5 above. This combination avoids production of $SO_2$ and the concomitent need for its recycle by oxidation to $SO_3$.

Use of devices promoting good mixing between the gas and liquid phases is desirable.

This reaction may be carried out in a molten salt reaction medium rather than in acids as solvents (so long as the stoichiometric requirements of the reaction are met), e.g. molten $KHSO_4$, $NaHSO_4$, $K_2S_2O_7$, $Na_3$-$BO_3$, etc. This process variation has certain potential advantages such as lower corrosivity, lower volatility, increased reaction medium inertness, and lower overall cost.

Second Step

This step is shown above as Eq. 2. It is an optional step and is carried out generally for the purpose of replacing the oxy-ester formed in the first step with an intermediate which is both reactive in the third step and does not substantially degrade the catalyst used in that later step. This step allows regeneration of the acid utilized in the first step for generation of the methyl ester.

The methyl ester may be separated from the first step reaction media by commonly practiced steps such as flashing or distillation. However, there is no need to isolate the methyl ester since solutions of the methyl ester and acid solvent react with added nucleophile to produce an intermediate which is reactive in the third step. The nucleophile in Eq. 2 is suitably then mixed with the methyl oxy-ester (pure or in the acid solvent) to produce a "methyl intermediate". By "methyl intermediate" is meant methanol, if the nucleophile is $H_2O$; methyl halide, if the nucleophile is a hydrogen halide such as HCl, HBr, or HI; methyl amino, if the nucleophile is $NH_3$; methyl thiol, if the nucleophile is $H_2S$, or acetonitrile if the nucleophile is HCN. Other nucleophiles can be utilized and would be known to the ordinary skilled worker but should be of a type not decomposed by reaction with the acid solvent. These reactions proceed readily to completion. An excess of the nucleophile is desirable. The preferred nucleophile is $H_2O$ since it may also be produced in the first step. The product methanol may be used directly or may be converted to a variety of hydrocarbons in a following step or steps.

Third Step

This step (shown above as Eq. 3) includes conversion of the methyl intermediate to a longer chain or higher molecular weight hydrocarbon.

Suitable processes for converting methanol and other methyl intermediates to higher molecular weight hydrocarbons are found in U.S. Pat. Nos. 3,894,107 and 3,979,472 to Butter et al. Butter shows the production of olefinic and aromatic compounds by contacting the methyl intermediate with an aluminosilicate catalyst, preferably HZSM-5, at a temperature between 650° F. and 1000° F.

Similarly, Butter suggests a process using a preferably catalyst of antimony oxide and HZSM-5 at a temperature between 250° C. and 700° C.

The ZSM-5 zeolite has been disclosed as a suitable molecular sieve catalyst for converting methyl alcohol into gasoline-range hydrocarbons. See, for instance, U.S. Pat. Nos. 3,702,886 to Argauer et al. and 3,928,483 to Chang et al.

Other processes include those described in U.S. Pat. No. 4,373,109 to Olah (bifunctional acid-base catalyzed conversion of methanol and other methyl intermediates into lower olefins); U.S. Pat. No. 4,687,875 to Currie et al. (metal coordination complexes of heteropolyacids as catalysts for converting short change aliphatic alcohols to short change hydrocarbons); U.S. Pat. No. 4,524,234 to Kaiser (production of hydrocarbons preferably from methanol using aluminophosphate molecular sieves); and U.S. Pat. No. 4,579,996 to Font Freide et al. (production of hydrocarbons from $C_1$ to $C_4$ monohaloalkanes using layered clays); etc. Each of the above is potentially suitable for the third step of this process and their contents are incorporated by notice.

Integrated Process

Where the process steps outlined as Eqs. 1-3 above are integrated, as might be done in an operating plant, $O_2$ is the oxidant and HY is a nucleophile, the overall process scheme is as follows:

$$CH_4 + \tfrac{1}{2}O_2 + HX \rightarrow CH_3X + H_2O$$

$$CH_3X + HY \rightarrow CH_3Y + HX$$

$$CH_3Y \rightarrow [CH_2] + HY$$

Net Reaction: $CH_4 + \tfrac{1}{2}O_2 \rightarrow [CH_2] + H_2O$

Where $H_2SO_4$ is both the oxidant and the acid and water is the nucleophile, the process for accomplishing the overall process is as follows:

$$CH_4 + 2H_2SO_4 \rightarrow CH_3OSO_3H + 2H_2O + SO_2$$

$$SO_2 + \tfrac{1}{2}O_2 + H_2O \rightarrow H_2SO_4$$

$$CH_3OSO_3H + H_2O \rightarrow CH_3OH + H_2SO_4$$

$$CH_3OH \rightarrow [CH_2] + H_2O$$

Net Reaction: $CH_4 + \tfrac{1}{2}O_2 \rightarrow [CH_2] + H_2O$

It should be understood that the first two reactions expressed immediately above are equivalent in sum to Eq. 1 of the overall process.

Where $SO_3$ is the oxidant, $H_2SO_4$ is the acid, and water is the nucleophile, the process for accomplishing the overall process is as follows:

$$CH_4 + SO_3 + H_2SO_4 \rightarrow CH_3OSO_3H + SO_2$$

$$SO_2 + \tfrac{1}{2}O_2 \rightarrow SO_3$$

$$CH_3OSO_3H + H_2O \rightarrow CH_3OH + H_2SO_4$$

$$CH_3OH \rightarrow [CH_2] + H_2O$$

Net Reaction: $CH_4 + \tfrac{1}{2}O_2 \rightarrow [CH_2] + H_2O$

It should be understood that the first two reactions expressed immediately above are equivalent in sum to Eq. 1 of the overall process. Where $O_2$ is the oxident, $CF_3SO_3H$ is the acid, and water is the nucleophile, the process is as follows:

$$CH_4 + \tfrac{1}{2}O_2 + CF_3SO_3H \rightarrow CH_3OSO_2CF_3 + H_2O$$

$$CH_3OSO_2CF_3 + H_2O \rightarrow CH_3OH + CF_3SO_3H$$

$$CH_3OH \rightarrow [CH_2] + H_2O$$

Net Reaction: $CH_4 + \tfrac{1}{2}O_2 \rightarrow [CH_2] + H_2O$

These reaction schemes permit regeneration and recycle of the acid and, in some instances, the auxiliary oxidant, which makes the process more economical. Some acids require additional steps to separate the nucleophile but such steps are known to the ordinarily skilled worker.

EXAMPLES

These examples are intended to show portions of the overall inventive process, in particular the alkyl esterification reaction utilizing methane as the reactant. The remainder of the process steps are easily selectable from known processes.

A. A 50 ml high pressure reactor was charged with 25 ml of 100% $H_2SO_4$ and 2.0 g of $HgSO_4$ (270 mM). The contents of the reactor were stirred, the reactor was flushed with methane and heated to 188° C. under 1800 psig of methane. After 1 hr the reactor was cooled to room temperature. A gas sample of the gas in the reactor was obtained for gas chromatographic analysis and an aliquot of the reaction mixture was qualitatively analyzed for methyl sulfate by $^{13}C$ NMR and $^1H$ NMR. A second aliquot was first diluted with 3 volumes of water and the resulting solution heated in a sealed container for 2 hrs. The resulting solution was quantitatively analyzed for free $CH_3OH$ by HPLC using an ion exclusion column with an eluant of 0.01% $H_2SO_4$ in $H_2O$ and a refractive index detector. Based on the high pressure liquid chromatography ("HPLC") and nuclear magnetic resonance ("NMR") analyses, the yield of methyl sufate was 746 mol % (25 mmoles, 1008 mM, Table I, entry 1) based on $HgSO_4$ added (assuming that the reaction proceeds via the Hg redox couple $Hg^{2+}/Hg_2^{2+}$). This corresponds to a productivity rate of $2.8 \times 10^{-7}$ mol. of oxy-ester/cc of reaction volume-sec based on the conversion of methane to methyl sulfate. Trace levels of acetic acid and dimethylether were detected. Gas chromatographic analysis showed that copious amounts of $SO_2$ and trace levels of $CO_2$ were produced.

B. To show the effect of $HgSO_4$ concentration, the general procedure of example A was repeated both with 1000 mM and 100 mM of $HgSO_4$ for 60 minutes under 510 psig of methane. The results shown in Table I (entries 2 and 3) show that the higher concentrations of $HgSO_4$ result in higher yields of methyl sulfate over the same reaction time.

C. To show the greater effectiveness of $Hg^{II}$ as compared to $Pd^{II}$, the general procedure of example A was repeated but with 165 mM of $PdSO_4$ and 100 mM $HgSO_4$ for 180 minutes under 400 psig of methane. The results shown in Table I (entries 4 and 5) show that, under identical conditions, the $HgSO_4$ system is about 17 times more active than the $PdSO_4$ system for the production of methyl sulfate.

D. As a "blank" run, the procedure of Example C was repeated but without added $PdSO_4$ or $HgSO_4$. As may be seen from the results in Table I (entry 6) no methyl sulfate was produced in the reaction.

E. To show the effect of acid concentration, the general procedure of Example A was twice repeated but with 90% (wt) $H_2SO_4$ (remainder $H_2O$) and 100% (wt) $H_2SO_4$, 100 mM $HgSO_4$, and 510 to 560 psig of methane for two hours. The results shown in Table I (entries 7 and 8) show that the yield of methyl sulfate was 464 mol % based on $HgSO_4$ added in the 100% $H_2SO_4$ and 155 mol % in the 90% $H_2SO_4$ system.

F. To show the effect of temperature, the general procedure of Example A was repeated at 140° C., 180° C., 180° C. and 200° C. with 100 mM $HgSO_4$ for two hours under 510 psig of methane. The results shown in Table I (entries 8, 9, 10 and 11) show that increasing temperatures from 140°–180° lead to increased yields of methyl sulfate. At 220° C., a loss in yield was observed.

G. To show the effect of methane pressure, the general procedure of Example A was repeated with 100 mM $HgSO_4$ at methane pressures from 360 psig to 1820 psig. The results shown in Table I (entries 12 and 13) show that the yield of methyl sulfate increases at higher pressures.

amount of methyl ester produced in entries 19-22 was less than the amount of metal present in the reaction medium (the metal could therefore be considered either a reactant or a catalyst), it was apparent that the use of oxygen to oxidize these metals would result in a process utilizing the metals in a truly catalytic fashion.

TABLE I

| Entry | Metal Salt | [Metal] (mM) | Acid | Temp (°C.) | Rxn Time (min) | [CH$_4$] (psig) | [CH$_3$OH] (mM) |
|---|---|---|---|---|---|---|---|
| 1 | HgSO$_4$ | 270 | H$_2$SO$_4$ | 180 (100%) | 60 | 1800 | 1008 |
| 2 | HgSO$_4$ | 100 | H$_2$SO$_4$ | 180 (100%) | 60 | 510 | 247 |
| 3 | HgSO$_4$ | 1000 | H$_2$SO$_4$ | 180 (100%) | 60 | 510 | 378 |
| 4 | PdSO$_4$ | 165 | H$_2$SO$_4$ | 180 (100%) | 180 | 400 | 50 |
| 5 | HgSO$_4$ | 100 | H$_2$SO$_4$ | 180 (100%) | 180 | 400 | 526 |
| 6 | — | — | H$_2$SO$_4$ | 180 (100%) | 180 | 400 | 0 |
| 7 | HgSO$_4$ | 100 | H$_2$SO$_4$ | 180 (90%) | 120 | 560 | 155 |
| 8 | HgSO$_4$ | 100 | H$_2$SO$_4$ | 180 (100%) | 120 | 510 | 464 |
| 9 | HgSO$_4$ | 100 | H$_2$SO$_4$ | 140 (100%) | 120 | 510 | 16 |
| 10 | HgSO$_4$ | 100 | H$_2$SO$_4$ | 160 (100%) | 120 | 510 | 121 |
| 11 | HgSO$_4$ | 100 | H$_2$SO$_4$ | 200 (100%) | 120 | 510 | 452 |
| 12 | HgSO$_4$ | 100 | H$_2$SO$_4$ | 180 (100%) | 60 | 360 | 187 |
| 13 | HgSO$_4$ | 100 | H$_2$SO$_4$ | 180 (100%) | 60 | 1820 | 394 |
| 14 | HgSO$_4$ | 100 | H$_4$P$_2$O$_7$ | 220 (100%) | 114 | 400 | 26 |
| 15 | HgO | 230 | CF$_3$SO$_3$H | 180 (100%) | 120 | 900 | 112 |
| 16 | Hg$^0$ | 155 | H$_2$SO$_4$ | 180 (100%) | 70 | 930 | 175 |
| 17 | HgCl$_2$ | 100 | H$_2$SO$_4$ | 180 (100%) | 180 | 900 | 16 |
| 18 | HgO | 155 | H$_2$SO$_4$ | 180 (100%) | 180 | 510 | 200 |
| 19 | Tl$_2$O$_3$ | 100 | CF$_3$SO$_3$H | 170 (100%) | 120 | 500 | 123 |
| 20 | Tl$_2$O$_3$ | 50 | H$_2$SO$_4$ | 180 (100%) | 180 | 400 | 38 |
| 21 | PtO$_2$ | 62 | H$_2$SO$_4$ | 180 (100%) | 185 | 400 | 48 |
| 22 | Au(OH)$_3$ | 100 | H$_2$SO$_4$ | 180 (100%) | 120 | 920 | 94 |
| 23 | Hg$_2$SO$_4$ | 51 | H$_2$SO$_4$ | 180 (100%) | 180 | 920 | 609 |

H. To show that the reaction proceeds in other acids, the general procedure of Example A was repeated in pyrophosphoric acid and trifluoromethanesulfonic acids. The results shown in Table I (entries 14 and 15) show that the reaction can be successfully carried out in pyrophosphoric acid and trifluoromethanesulfonic acids.

I. To show that the reaction proceeds with different forms of Hg, the general procedure of Example A was repeated variously using HgO, HgCl$_2$, Hg$_2$SO$_4$, and Hg metal in place of HgSO$_4$. The results shown in Table I (entries 16, 17, 18, and 23) show that these forms of Hg also leads to formation of methyl esters.

J. To show that other class "B" metals and/or Pearson "soft" metal ions can be utilized in our process for the selective oxidation of methane, the general procedure of Example A was repeated variously using the metals shown in Table I (entries 19-22). The metals Tl, Pt, and Au successfully facilitated the oxidation of methane to the methyl esters. Although the molar The invention has been shown both by description and by example. The examples are only examples; they should not be used in any fashion to limit the scope of the invention otherwise described here.

Additionally, it should be clear that one having ordinary skill in this art would envision equivalents to the processes described in the claims that follow and these equivalents would be within the scope and spirit of the claimed invention.

We claim as our invention:

1. A process for converting one or more lower alkanes to higher molecular weight hydrocarbons comprising the steps of:

a. contacting one or more lower alkanes, an oxidizing agent, an oxidation resistant acid with a Pka<2.0, and a catalyst in at least a catalytic amount comprising one or more metals selected from the group consisting of the class "B" metals of the Mendeleev Table of elements and Pearson "soft" and "borderline" metal cations at esterification conditions to produce a lower alkyl oxy-ester of the acid in a molar amount greater than the molar amount of the metal, b. converting the lower alkyl oxy-ester of the acid to an alkyl intermediate, and c. catalytically converting the alkyl intermediate to higher molecular weight hydrocarbons.

2. The process of claim 1 where the lower alkane comprises methane.

3. The process of claim 2 where the alkyl intermediate comprises methanol.

4. The process of claim 1 where the lower alkane comprises ethane, propane, or butane.

5. The process of claim 2 where the oxidizing agent is selected from the group consisting of halogens ($F_2$, $Cl_2$, $Br_2$, $I_2$), $HNO_3$, perchloric acid, hypochlorites, peroxy compounds ($H_2O_2$, $CH_3CO_3H$, $K_2S_2O_8$), $O_2$ or $O_3$, $SO_3$, $NO_2$, $H_2SO_4$, and cyanogen.

6. The process of claim 2 where the oxidation is conducted at the anode of an electrochemical cell.

7. The process of claim 5 where the oxidizing agent is $O_2$.

8. The process of claim 5 where the oxidizing agent is $SO_3$.

9. The process of claim 5 where the oxidizing agent is $H_2SO_4$.

10. The process of claim 2 where the acid is selected from the group consisting of $HNO_3$, $H_2SO_4$, $CF_3CO_2H$, $CF_3SO_3H$, $H_3PO_4$, HPA's (heteropolyacids), $B(OH)_3$, anhydrides of these acids such as $H_4P_2O_7$, $H_2S_2O_7$, and mixtures of two or more of these acids or these acids and anhydrides.

11. The process of claim 10 where the acid is $H_2SO_4$.

12. The process of claim 10 where the acid is $CF_3SO_3H$.

13. The process of claim 5 where the acid is $CF_3SO_3H$.

14. The process of claim 5 where the acid is $H_2SO_4$.

15. The process of claim 2 where the catalytic metal is selected from the group consisting of Pd, Tl, Pt, Hg, and Au.

16. The process of claim 12 where the catalytic metal is Hg.

17. The process of claim 13 where the catalytic metal is selected from the group consisting of Pd, Tl, Pt, Hg, and Au.

18. The process of claim 17 where the catalytic metal is Hg.

19. The process of claim 14 where the catalytic metal is selected from the group consisting of Pd, Tl, Pt, Hg, and Au.

20. The process of claim 19 where the catalytic metal is Hg.

21. The process of claim 5 where the catalytic metal is Hg.

22. The process of claim 11 where the catalytic metal is Hg.

23. The process of claim 12 where the catalytic metal is Hg.

24. The process of claim 5 where the methyl intermediate is methanol.

25. The process of claim 6 where the methyl intermediate is methanol.

26. The process of claim 11 where the methyl intermediate is methanol.

27. The process of claim 12 where the methyl intermediate is methanol.

28. The process of claim 24 additionally comprising the step of converting methanol to higher molecular weight hydrocarbons.

29. A process for esterifying one or more lower alkanes comprising the steps of:

a. contacting the one or more lower alkanes, oxidizing agent, a strong mineral acid, and a catalyst in at least a catalytic amount comprising a catalytic metal selected from the group consisting of Pd, Tl, Pt, Hg, and Au at esterification conditions to produce a lower alkyl oxy-ester of the acid in a molar amount greater than the molar amount of the catalytic metal, and b. recovering the lower alkyl oxy-ester of the acid.

30. The process of claim 29 where the lower alkane comprises methane.

31. The process of claim 30 hwere the oxidizing agent is selected from the group consisting of halogens ($F_2$, $Cl_2$, $Br_2$, $I_2$), $HNO_3$, perchloric acid, hypochlorites, peroxy compounds ($H_2O_2$, $CH_3CO_3H$, $K_2S_2O_8$), $O_2$ or $O_3$, $SO_3$, $NO_2$, $H_2SO_4$, and cyanogen.

32. The process of claim 31 where the oxidizing agent is $O_2$.

33. The process of claim 31 where the oxidizing agent is $SO_3$.

34. The process of claim 31 where the oxidizing agent is $H_2SO_4$.

35. The process of claim 31 where the acid is selected from the group consisting, $HNO_3$, $H_2SO_4$, $CF_3CO_2H$, $CF_3SO_3H$, $H_3PO_4$, HPA's (heteropolyacids), $B(OH)_3$ or the like, anhydrides of these acids such as $H_4P_2O_7$, $H_2S_2O_7$ or the like, and mixtures of two or more of these acids or these acids and anhydrides.

36. The process of claim 35 where the acid is $H_2SO_4$.

37. The process of claim 35 where the acid is $CF_3SO_3H$.

38. The process of claim 32 where the acid is $CF_3SO_3H$.

39. The process of claim 31 where the catalytic metal is Hg or Tl.

40. The process of claim 35 where the catalytic metal is Hg.

41. The process of claim 38 where the catalytic metal is Hg.

42. The process of claim 39 where the catalytic metal is Hg.

43. In a process for the catalytic oxidation of hydrocarbonaceous feeds with an oxidizing agent to produce oxyesters or partially oxidized derivatives of the hydrocarbonaceous feed, the improvement wherein $H_2SO_4$, $SO_3$ or mixtures thereof are the oxidizing agent.

44. The process of claim 43 where the hydrocarbonaceous feed is selected from the group consisting of aromatics, alkanes, alkenes, alkynes, alkyl aromatics, and alkenyl aromatics.

45. The process of claim 43 where $H_2SO_4$ is the oxidizing agent.

46. The process of claim 43 where $SO_3$ is the oxidizing agent.

47. The process of claim 43 where a mixture of $SO_3$ and $H_2SO_4$ is the oxidizing agent.

48. The process of claim 44 where the hydrocarbonaceous feed comprises one or more lower alkanes.

49. In a process for the catalytic oxidation of lower alkanes with an oxidizing agent to produce oxyesters or partially oxidized lower alkane derivatives, the improvement wherein $H_2SO_4$, $SO_3$ or mixtures thereof are the oxidizing agent.

50. The process of claim 49 where the catalytic oxidation produces an oxy-ester.

51. The process of claim 49 where the lower alkane comprises methane.

52. In a process for the conversion of hydrocarbonaceous feeds to comparatively higher molecular weight hydrocarbons, wherein the hydrocarbonaceous feed is catalytically oxidized with an oxidizing agent to produce an oxy-ester and the oxy-ester so obtained is then reacted with a nucleophile to yield a functional intermediate followed by catalytic conversion of the functional intermediate to the higher molecular weight hydrocarbons, the improvement wherein $H_2SO_4$, $SO_3$, or mixtures thereof are the oxidizing agent.

53. The process claim 52 where the hydrocarbonaceous feed is selected from the group consisting of aromatics, alkanes, alkenes, alkynes, alkyl aromatics, and alkenyl aromatics.

54. The process of claim 52 where $H_2SO_4$ is the oxidizing agent.

55. The process of claim 52 where $SO_3$ is the oxidizing agent.

56. The process of claim 52 where a mixture of $SO_3$ and $H_2SO_4$ is the oxidizing agent.

57. The process of claim 53 where the hydrocarbonaceous feed comprises one or more lower alkanes.

58. The process of claim 57 where the hydrocarbonaceous feed comprises methane.

* * * * *